United States Patent [19]

Parg et al.

[11] Patent Number: 4,523,034
[45] Date of Patent: Jun. 11, 1985

[54] HERBICIDAL DIPHENYL ETHERS, THEIR PREPARATION AND THEIR USE AS HERBICIDES

[75] Inventors: Adolf Parg, Bad Durkheim; Gerhard Hamprecht, Weinheim; Bruno Wuerzer, Otterstadt, all of Fed. Rep. of Germany

[73] Assignee: BASF Aktiengesellschaft, Fed. Rep. of Germany

[21] Appl. No.: 356,736

[22] Filed: Mar. 10, 1982

[30] Foreign Application Priority Data

Apr. 8, 1981 [DE] Fed. Rep. of Germany ........ 3114072

[51] Int. Cl.$^3$ ..................... C07C 143/86; A01N 41/00
[52] U.S. Cl. ........................................ 564/79; 71/103; 71/105; 71/116; 260/465 D; 260/465 E; 562/430
[58] Field of Search ............... 260/465 D, 465 E; 562/430; 564/79

[56] References Cited

U.S. PATENT DOCUMENTS 3,531,523  9/1970  Nelson et al. ...................... 564/79

FOREIGN PATENT DOCUMENTS 10249   8/1979  European Pat. Off. .
0023725 2/1981  European Pat. Off. .
2261918 6/1973  Fed. Rep. of Germany .
2304006 8/1973  Fed. Rep. of Germany .
2311638 9/1973  Fed. Rep. of Germany .
2001635 2/1979  United Kingdom .

OTHER PUBLICATIONS

Chemical Abstracts, vol. 76, (1972), No. 158359c.

Primary Examiner—Thomas A. Waltz
Attorney, Agent, or Firm—Keil & Weinkauf

[57] ABSTRACT

Diphenyl ethers of the formula

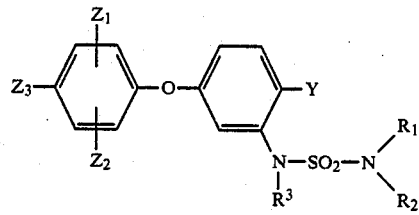

where $Z_1$ and $Z_2$ are each hydrogen, halogen, nitro, cyano, carboxyl, alkyl, haloalkyl or alkoxy, $Z_3$ is halogen, nitro, cyano, alkyl, haloalkyl, alkoxy, haloalkoxy, alkylmercapto, haloalkylmercapto, alkylsulfinyl, haloalkylsulfinyl, alkylsulfonyl or haloalkylsulfonyl, Y is halogen, cyano or nitro, $R_1$ is hydrogen, alkyl, cycloalkyl, alkoxy, haloalkyl or alkoxyalkyl, $R_2$ is hydrogen, alkyl, acyl or an alkali metal atom and $R_3$ is hydrogen, alkyl or an alkali metal atom, and herbicides containing these compounds.

5 Claims, No Drawings

HERBICIDAL DIPHENYL ETHERS, THEIR PREPARATION AND THEIR USE AS HERBICIDES

The present invention relates to diphenyl ethers, a process for their preparation, herbicides containing these compounds as active ingredients, and a process for controlling undesirable plant growth using these active ingredients.

The use, as herbicides, of diphenyl ethers having a substituted amino group, eg. 2-chloro-4-trifluoromethyl-3'-methylamino-4'-nitrodiphenyl ether (German Laid-Open Application DOS No. 2,304,006) or 2-chloro-4-trifluoromethyl-3'-chloroacetylamido-4'-nitrodiphenyl ether (German Laid-Open Application DOS No. 2,311,638), has been disclosed.

Further, the use of diphenyl ethers having a substituted sulfonamido group, eg. 2,4,6-trichloro-3'-N,N-dimethylsulfonamido-4'-nitro-diphenyl ether (German Laid-Open Application DOS No. 2,261,918, British Patent No. 2,001,635 and European Laid-Open Application No. 23,725), has been disclosed.

We have found that the novel diphenyl ethers of the formula I

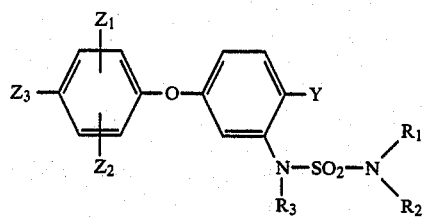

where $Z_1$ and $Z_2$ independently of one another are each hydrogen, halogen, nitro, cyano, carboxyl, lower alkyl, lower haloalkyl or lower alkoxy, $Z_3$ is halogen, nitro, cyano, lower alkyl, lower haloalkyl, lower alkoxy, lower haloalkoxy, lower alkylmercapto, lower haloalkylmercapto, lower alkylsulfinyl, lower haloalkylsulfinyl, lower alkylsulfonyl or lower haloalkylsulfonyl, Y is halogen, cyano or nitro, $R_1$ is hydrogen, lower alkyl, cycloalkyl, lower alkoxy, lower haloalkyl or lower alkoxyalkyl, $R_2$ is hydrogen, lower alkyl, acyl or an alkali metal atom and $R_3$ is hydrogen, lower alkyl or an alkali metal atom, have a very good herbicidal and, with regard to crop plants, selective herbicidal action.

In formula I, $Z_1$ and $Z_2$ can independently of one another each be, for example, hydrogen, fluorine, chlorine, bromine, iodine, nitro, cyano, carboxyl, methyl, ethyl, n-propyl, i-propyl, n-butyl, tert.-butyl, trifluoromethyl, difluoromethyl, fluoromethyl, trichloromethyl, dichloromethyl, chloromethyl, difluorochloromethyl, 1-chloroethyl, 2-chloroethyl, 1-fluoroethyl, 2-fluoroethyl, 2,2,2-trichloroethyl, 2,2,2-trifluoroethyl, 1,1,2,2-tetrafluoroethyl, 1,1,2-trifluoro-2-chloroethyl, 1,1,2,2,2-pentafluoroethyl, methoxy, ethoxy, n-propoxy, i-propoxy or tert.-butoxy, $Z_3$ can be fluorine, chlorine, bromine, iodine, nitro, cyano, methyl, ethyl, n-propyl, i-propyl, n-butyl, tert.-butyl, trifluoromethyl, difluoromethyl, fluoromethyl, trichloromethyl, dichloromethyl, chloromethyl, difluorochloromethyl, 1-chloroethyl, 2-chloroethyl, 1-fluoroethyl, 2-fluoroethyl, 2,2,2-trichloroethyl, 2,2,2-trifluoroethyl, 1,1,2,2-tetrafluoroethyl, 1,1,2-trifluoro-2-chloroethyl, 1,1,2,2,2-pentafluoroethyl, methoxy, ethoxy, n-propoxy, i-propoxy, tert.-butoxy, trichloromethoxy, trifluoromethoxy, 1-chloroethoxy, 2-chloroethoxy, 1-fluoroethoxy, 2-fluoroethoxy, 2,2,2-trichloroethoxy, 2,2,2-trifluoroethoxy, 1,1,2,2-tetrafluoroethoxy, 1,1,2,2,2-pentafluoroethoxy, methylmercapto, ethylmercapto, trichloromethylmercapto, trifluoromethylmercapto, methylsulfinyl, ethylsulfinyl, methylsulfonyl, ethylsulfonyl or trifluoromethylsulfonyl, Y can, for example, be fluorine, chlorine, bromine, iodine, cyano or nitro, $R_1$ can, for example, be hydrogen, methyl, ethyl, n-propyl, iso-propyl, n-butyl, iso-butyl, tert.-butyl, n-pentyl, n-hexyl, n-heptyl, 1,2-dimethylbutyl, 1,3-dimethylbutyl, 3-chloropentyl, 3-chloropropyl, 2-chloroethyl, 2-fluoroethyl, 1-chloropropyl, 2-chloropropyl, 1-fluoroethyl, 2-fluoroethyl, 1-fluoropropyl, cyclopentyl, cyclohexyl, methoxy, ethoxy, propoxy, isopropoxy, n-butoxy, n-pentoxy, methoxymethyl, ethoxymethyl or methoxyethyl, $R_2$ can be hydrogen, methyl, ethyl, n-propyl, iso-propyl, acetyl, chloroacetyl, benzoyl, sodium or potassium and $R_3$ can be hydrogen, methyl, ethyl, propyl, sodium or potassium.

Preferred diphenyl ethers are compounds of the formula I where $Z_1$ and $Z_2$ independently of one another are each hydrogen, chlorine, bromine or cyano, $Z_3$ is chlorine, bromine, methyl or, in particular, trifluoromethyl, Y is nitro, $R_1$ and $R_2$ are each hydrogen or lower alkyl and $R_3$ is hydrogen.

The compounds of formula I can be prepared, for example, by the following process:

The diphenyl ether of the general formula II

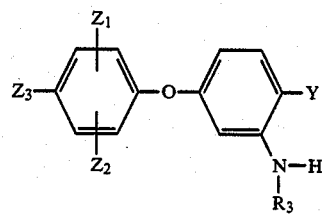

where $Z_1$, $Z_2$, $Z_3$, $R_3$ and Y have the above meanings, is reacted with a sulfamyl halide of the general formula III

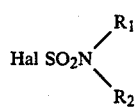

where $R_1$ and $R_2$ have the above meanings and Hal is halogen, in an inert organic solvent, with or without the addition of an acid acceptor, at from $-80°$ C. to $+100°$ C., advantageously at from $-40°$ C. to $+60°$ C., under atmospheric or superatmospheric pressure, continuously or batchwise, to give a compound of the formula I.

The process can be represented, for example, by the following equation:

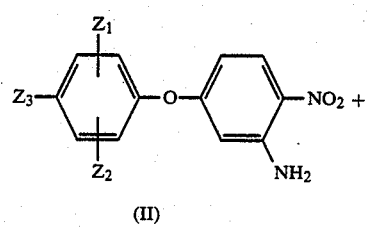

(II)

(III)

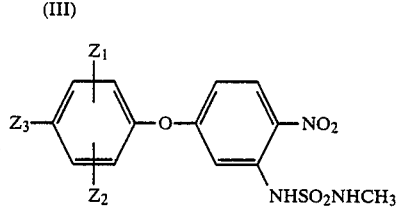

The starting materials are reacted, for example, in about stoichiometric amounts, ie. starting material III can be employed, for example, in an excess of up to 20 mole %, based on II.

An acid acceptor can be added to complete the reaction. For example, the process is carried out by simultaneously adding a solution of the sulfamyl chloride III in an organic solvent, at from −80° C. to −40° C., and an equimolar amount of an acid acceptor to a solution of the diphenyl ether II in an inert organic solvent. To complete the reaction, stirring is continued for from 0.5 to 48 hours, preferably for from 2 to 12 hours, at from 0° C. to 30° C. The reaction mixture is concentrated, and the desired product can be isolated by reprecipitation or recrystallization or by stirring the mixture with water, and can be purified, if required, by chromatography.

Organic solvents which are inert under the particular reaction conditions are used for the reaction. Examples of suitable solvents are halohydrocarbons, in particular chlorohydrocarbons, eg. tetrachloroethylene, 1,1,2,2-tetrachloroethane, 1,1,1,2-tetrachloroethane, dichloropropane, methylene chloride, dichlorobutane, chloroform, chloronaphthalene, dichloronaphthalene, carbon tetrachloride, 1,1,1-trichloroethane, 1,1,2-trichloroethane, trichloroethylene, pentachloroethane, o-, m- and p-difluorobenzene, 1,2-dichloroethane, 1,1-dichloroethane, cis-1,2-dichloroethylene, chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene, ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane and β,β'-dichlorodiethyl ether, nitrohydrocarbons, eg. nitromethane, nitroethane, nitrobenzene, o-, m- and p-chloronitrobenzene and o-nitrotoluene, nitriles, eg. acetonitrile, butyronitrile, isobutyronitrile, benzonitrile and m-chlorobenzonitrile, aliphatic or cycloaliphatic hydrocarbons, eg. heptane, pinane, nonane, o-, m- and p-cymene, gasoline fractions of boiling points from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane, esters, eg. ethyl acetate, acetoacetates and isobutyl acetate, amides, eg. formamide, methylformamide and dimethylformamide, and ketones, eg. acetone and methyl ethyl ketone, and mixtures of the above. The amount of solvent used is advantageously from 100 to 2,000% by weight, preferably from 200 to 700% by weight, based on the starting materials.

All conventional acid acceptors can be used. These preferably include tertiary amines, alkaline earth metal compounds, ammonium compounds and alkali metal compounds, and mixtures of these, but zinc compounds can also be used. For example, the following basic compounds are suitable: potassium hydroxide, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, diisopropylethylamine, trihexylamine, N,N-dimethylaniline, N,N-diethylaniline, N,N-dipropyltoluidine, N,N-dimethyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, n-propyldiisopropylamine, N,N'-dimethylcyclohexylamine, 2,6-lutidine, 2,4-lutidine, trifurylamine and triethylenediamine.

The starting compounds can be prepared by conventional methods. Thus, the diphenyl ethers of the general formula II can be prepared, for example, by the procedure described in German Laid-Open Application DOS No. 2,926,829, and the sulfamyl halides can be prepared by the methods described, for example, in German Laid-Open Application DOS No. 2,164,176.

The Examples which follow illustrate the preparation of the compounds of the formula I by the process given. Parts by weight bear the same relation to parts by volume as that of the kilogram to the liter.

EXAMPLE 1

15.7 parts by weight of isopropylamidosulfonyl chloride and, at the same time, 10.1 parts by weight of triethylamine were added dropwise to a solution of 33.3 parts by weight of 3-(2'-chloro-4'-trifluoromethylphenoxy)-6-nitroaniline in 200 parts by volume of absolute ether at from −60° C. to −40° C. The reaction mixture was first slowly warmed to room temperature, stirred for two hours at 30° C., and then filtered under suction. The organic phase was treated successively with dilute hydrochloric acid, aqueous sodium bicarbonate solution and water, dried with magnesium sulfate, filtered off from solid material, and concentrated. 36 parts by weight (85% of theory) of N-(3-(2'-chloro-4'-trifluoromethylphenoxy)-6-nitrophenyl) N'-isopropyl sulfamide (Compound No. 1) of refractive index $n_D^{25}$: 1.5748, of the formula

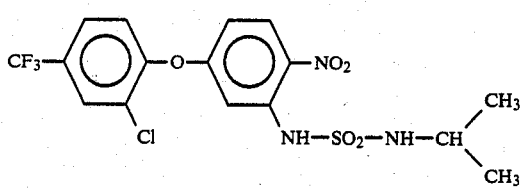

were obtained.

EXAMPLE 2

10 parts by weight of N-(3-(2'-chloro-4'-trifluoromethylphenoxy)-6-nitrophenyl) N'-isopropyl sulfamide were dissolved in 100 parts by volume of absolute methanol, 4 parts by weight of a 30% strength methanolic sodium methylate solution were added, and the solution was concentrated to dryness under reduced pressure. 10 parts by weight of sodium N-(3-(2'-chloro-4'-trifluoromethylphenoxy)-6-nitrophenyl) N'-isopropyl sulfamide (Compound No. 2), which decomposes at 160° C. and has the formula

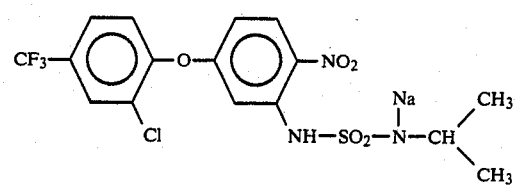

were obtained. For example, the following compounds of the formula I can be prepared in a corresponding manner.

| No. | $Z_2$ | Y | $R_3$ | $R_2$ | $R_1$ | M.p. (°C.), $n_D^{25}$ Wavelength of a band in the spectrum |
|---|---|---|---|---|---|---|
| 3 | 2-Chloro-4-trifluoromethylphenoxy | NO₂ | H | H | H | 130–135 |
| 4 | " | " | " | " | Methyl | 1.5501 |
| 5 | " | " | " | Methyl | " | |
| 6 | " | " | " | H | Ethyl | |
| 7 | " | " | " | " | n-Propyl | |
| 8 | " | " | " | " | n-Butyl | 60–65 |
| 9 | " | " | " | " | n-Pentyl | |
| 10 | " | " | " | " | Cyclohexyl | 1.5678 |
| 11 | " | " | " | " | Methoxy | |
| 12 | " | " | " | " | Isopropoxy | |
| 13 | " | " | " | Acetyl | Methyl | |
| 14 | " | " | CH₃ | H | " | |
| 15 | " | " | " | Methyl | " | |
| 16 | " | Br | H | H | H | |
| 17 | " | " | " | " | Methyl | |
| 18 | " | " | " | " | Isopropyl | |
| 19 | " | CN | " | " | Methyl | |
| 20 | 2,4-Dichlorophenoxy | NO₂ | " | " | H | |
| 21 | " | " | " | " | Methyl | 1.637 |
| 22 | " | " | " | " | iso-Propyl | 105–112 |
| 23 | " | " | " | Methyl | Methyl | |
| 24 | 2,4-Dibromophenoxy | " | " | H | H | |
| 25 | " | " | " | " | Methyl | |
| 26 | " | " | " | " | iso-Propyl | |
| 27 | 3-Chloro-4-trifluoromethylphenoxy | " | " | " | " | |
| 28 | " | " | " | " | Methyl | |
| 29 | " | " | " | " | iso-Propyl | |
| 30 | 2,6-Dichloro-4-trifluoromethylphenoxy | " | " | " | H | |
| 31 | " | " | " | " | Methyl | |
| 32 | " | " | " | " | iso-Propyl | |
| 33 | 2-Chloro-4-methylphenoxy | " | " | " | Methyl | |
| 34 | 2-Chloro-4-trifluoromethoxyphenoxy | " | " | " | " | |
| 35 | " | " | " | " | iso-Propyl | |
| 36 | 2-Chloro-4-trifluoromethylmercaptophenoxy | " | " | " | H | |
| 37 | 2-Chloro-4-trifluoromethylmercapto-phenoxy | " | " | " | Methyl | |
| 38 | " | " | " | " | iso-Propyl | |
| 39 | 2-Chloro-4-trifluoromethylphenoxy | " | " | " | 2-Chloroethyl | 92–94 |
| 40 | 2,4-Dichlorophenoxy | " | " | " | " | 88–91 |
| 41 | 2-Chloro-4-trifluoromethylphenoxy | " | CH₃ | CH₃ | iso-Propyl | |

The active ingredients can be converted into the conventional formulations, e.g. solutions, emulsions, suspensions, dusts, powders, pastes and granules. The form of application depends entirely on the purpose for which the agents being used; it should, however, ensure a fine and uniform distribution of the active ingredient. The formulations are prepared in conventional manner, for example by diluting the active ingredient with solvents and/or carriers, with or without the addition of emulsifiers and dispersants and, where water is used as the diluent, with or without organic auxiliary solvents. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines, e.g. ethanolamine, dimethylformamide, and water; solid carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The herbicidal agents contain from 0.1 to 95% by weight of active ingredients, preferably from 0.5 to 90%.

The agents, and the ready-to-use preparations obtained therefrom, e.g., solutions, emulsions, suspensions, powders, dusts, pastes or granules, are applied in conventional manner, e.g. by spraying, atomizing, dusting, broadcasting, treating seed or watering.

Examples of such formulations are given below.

EXAMPLE I 90 parts by weight of compound 1 is mixed with 10 parts by weight of N-methyl-alpha-pyrrolidone. A mixture is obtained which is suitable for application in the form of very fine drops.

EXAMPLE II 10 parts by weight of compound 2 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

EXAMPLE III 20 parts by weight of compound 2 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

EXAMPLE IV 20 parts by weight of compound 3 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil.

EXAMPLE V 80 parts by weight of compound 1 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 70 parts by weight of powdered silica gel, and triturated in a hammer mill.

EXAMPLE VI 5 parts by weight of compound 1 is initimately mixed with 95 parts by weight of particulate kaolin. A dust is obtained containing 5% by weight of the active ingredient.

EXAMPLE VII 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE VIII 40 parts by weight of compound 1 is intimately mixed with 10 parts of the sodium salt of a phenolsulfonic acid-urea-formaldehyde condensate, 2 parts of silica gel and 48 parts of water to give a stable aqueous dispersion.

EXAMPLE IX 20 parts of compound 1 is intimately mixed with 12 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

Application may be pre- or postemergence. Preferably, the novel active ingredients are applied after emergence of the unwanted plants, both on cropland and uncropped land. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

Depending on the season and the growth stage of the plants, the amounts of active ingredient applied vary from 0.025 to 15 kg/ha and more.

The influence of various representatives of the novel herbicidal diphenyl ethers on the growth of unwanted and crop plants is demonstrated in the greenhouse experiments.

The vessels employed were plastic flowerpots having a volume of 300 cm$^3$, and which were filled with a sandy loam containing about 1.5% humus. The seeds of the test plants were sown shallow, and separately, according to species.

In the preemergence treatment, the active ingredients were then immediately applied to the surface of the soil as a suspension or emulsion in water by spraying through finely distributing nozzles. The amount of active ingredient applied in this treatment was equivalent to 3.0 kg/ha.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown separately as seedlings and transplanted to the experiment vessels a few days before treatment. The amounts of active ingredient applied in this treatment varied, and were either 0.125 or 0.06 kg/ha. A rate of 3.0 kg/ha of active ingredient was also used.

The following prior art compounds were used for comparison purposes:

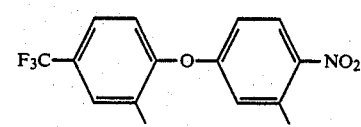

at 0.125 kg/ha

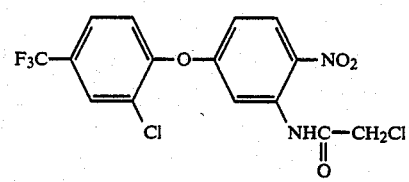

at 0.5 kg/ha.

No cover was placed on the vessels in the postemergence treatment.

The pots were set up in the greenhouse—species from warmer areas at from 20° to 35° C., and species from moderate climates at 10° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

In investigations into the herbicidal action on postemergence application in the greenhouse at a rate of 3.0 kg/ha, novel compounds 4, 3 and 2 exhibited a very good action.

In investigations into the selective herbicidal action on postemergence application in the greenhouse, active ingredient no. 4, at 0.125 kg/ha, had a very good herbicidal action on various broadleaved weed species and was much better tolerated by cereals than the prior art comparative compounds A and B.

The selectivity of the compound according to the invention was good, whereas the damage caused by the comparative compounds was very heavy and no longer acceptable; for this reason, their good herbicidal action is of little use for this application.

In investigations into the selective herbical action on postemergence application in the greenhouse, active ingredient no. 4 was well tolerated by sunflowers and had an excellent herbicidal action.

Also in greenhouse experiments, active ingredient no. 39, applied postemergence at rates of 0.06 and 0.125 kg/ha, combated broadleaved weeds very well without causing any (or only slight and temporary) damage to the crop plant sunflowers.

In further greenhouse experiments, compounds nos. 8, 10, 22, 21, 40 and 41, at 3.0 kg/ha, had a herbicidal action on unwanted plants.

In view of the many application methods possible (preemergence, postemergence, post-directed spraying), the active ingredients may be used in numerous crops, for example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape seed |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum | parsley |
| spp. tuberosum | |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |

| Botanical name | Common name |
| --- | --- |
| *Triticum aestivum* | wheat |
| *Vaccinium corymbosum* | blueberries |
| *Vaccinium vitis-idaea* | cranberries |
| *Vicia faba* | tick beans |
| *Vigna sinensis (V. unguiculata)* | cow peas |
| *Vitis vinifera* | grapes |
| *Zea mays* | Indian corn, sweet corn, maize |

To increase the spectrum of action and to achieve synergistic effects, the novel diphenyl ether derivatives may be mixed among themselves, or mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, other diphenyl ethers, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with mineral salt solutions used to remedy nutritional or trace element deficiencies. Non-phytotoxic oils and oil concentrates may also be added.

We claim:

1. A diphenyl ether of the formula

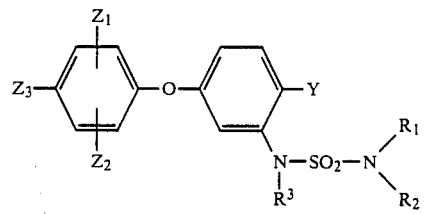

where $Z_1$ and $Z_2$ independently of one another are each hydrogen, halogen, nitro, cyano, carboxyl, lower alkyl, lower haloalkyl or lower alkoxy, $Z_3$ is halogen, nitro, cyano, lower alkyl, lower haloalkyl, lower alkoxy, lower haloalkyl, lower alkylmercapto, lower haloalkylmercapto, lower alkylsulfinyl, lower haloalkylsulfinyl, lower alkylsulfonyl or lower haloalkylsulfonyl, Y is cyano or nitro, $R_1$ is hydrogen, lower alkyl, cycloalkyl, lower alkoxy, lower haloalkyl or lower alkoxyalkyl, $R_2$ is hydrogen, lower alkyl, acyl or an alkali metal atom and $R_3$ is hydrogen, lower alkyl or an alkali metal atom.

2. A diphenyl ether selected from the group consisting of N-3-(2'-chloro-4'-trifluoromethylphenoxy)-6-nitrophenyl-sulfamide, N-3-(2'-chloro-4'-trifluoromethylphenoxy)-6-nitrophenyl-N'-methyl-sulfamide and N-3-(2'-chloro-4'-trifluoromethylphenoxy)-6-nitrophenyl-N'-isopropyl-sulfamide.

3. A diphenyl ether as described in claim 1 wherein $Z_1$ and $Z_2$ independently of one another are each hydrogen, chlorine, bromine or cyano, $Z_3$ is chlorine, bromine, methyl or trifluoromethyl, Y is nitro, $R_1$ and $R_2$ are each hydrogen or lower alkyl and $R_3$ is hydrogen.

4. A diphenyl ether as set forth in claim 3 wherein $Z_3$ is trifluoromethyl.

5. A diphenyl ether as described in claim 1, wherein $Z^1$ and $Z^2$ are hydrogen or halogen, $Z^3$ is halogen or lower haloalkyl, Y is nitro, $R^1$ is hydrogen, lower alkyl, cyclopentyl, cyclohexyl or lower haloalkyl, $R^2$ is hydrogen or lower alkyl or an alkali metal atom, and $R^3$ is hydrogen or lower alkyl.

* * * * *